United States Patent [19]

Ohnishi et al.

[11] Patent Number: 4,476,127

[45] Date of Patent: Oct. 9, 1984

[54] 7-DIETHYLAMINO-5-METHYL-THIAZOLO[5,4-d]PYRIMIDINE AND PHARMACEUTICAL COMPOSITION CONTAINING SAME

[75] Inventors: Haruo Ohnishi, Chiba; Hiroshi Kosuzume, Yokohama; Yasuo Suzuki, Kawaguchi; Ei Mochida, Toshima, all of Japan

[73] Assignee: Mochida Pharmaceutical Co., Ltd., Tokyo, Japan

[21] Appl. No.: 433,206

[22] PCT Filed: Sep. 19, 1982

PCT No.: PCT/JP82/00046

§ 371 Date: Sep. 29, 1982

§ 102(e) Date: Sep. 29, 1982

[87] PCT Pub. No.: WO83/02945

PCT Pub. Date: Sep. 1, 1983

[51] Int. Cl.$^3$ .................. A61K 31/495; C07D 417/02
[52] U.S. Cl. ..................................... 424/250; 544/255
[58] Field of Search ........................ 544/255; 424/250

[56] References Cited

U.S. PATENT DOCUMENTS 2,933,498  4/1960  Hitchings et al. .................. 544/255
3,850,917  11/1974  Muller et al. ...................... 544/255

FOREIGN PATENT DOCUMENTS 35591  2/1982  Japan .
713652  8/1954  United Kingdom .

OTHER PUBLICATIONS

Robins et al., J. Am. Chem. Soc. 79, pp. 490–494 (1957) Potential Purine Antagonists. p. 491, Compound XIII.

Primary Examiner—Donald G. Daus
Assistant Examiner—Cecilia Shen
Attorney, Agent, or Firm—Parkhurst & Oliff

[57] ABSTRACT

The compound related to this invention is 7-diethylamino-5-methyl-thiazolo[5,4-d]pyrimidine.

The compound related to this invention possesses vasodilating action, hypotensive action, inhibitory action on platelet aggregation, and lowering action on cholesterol levels in blood, and is useful as a therapeutic agent for cardiovascular diseases.

2 Claims, No Drawings

7-DIETHYLAMINO-5-METHYL-THIAZOLO[5,4-d]PYRIMIDINE AND PHARMACEUTICAL COMPOSITION CONTAINING SAME

TECHNICAL FIELD

The present invention relates to a novel thiazolopyrimidine derivative having vasodilating action, hypotensive action, inhibitory action on platelet aggregation, and reducing action on cholesterol level in blood.

BACKGROUND ART

Cardiovascular diseases, for example ischemic heart diseases, cerebrovascular diseases, atherosclerosis and hypertension, together with malignant tumors, are quite important diseases as major causes of death. Among these cardiovascular diseases, ischemic heart diseases and insufficiency of cerebral or peripheral circulation are generally understood to be caused by a lack of nutrition and oxygen supply, which is originally caused by insufficient blood flow resulting from arterial thrombus formation or from atherosclerosis. Therefore, the kind of drug which improves blood flow of the affected organ based on vasodilating action on the ischemic area, such as coronary arteries, is effective in the treatment of these diseases. Also, the kind of drug that inhibits platelet aggregation, which is a cause of arterial thrombus formation, or drug that reduces elevated serum cholesterol, which causes atherosclerosis, is understood to be effective in preventing pathogenesis of these diseasess.

Vasodilators, for example hydralazine, show hypotensive activity and have been frequently used in the treatment of hypertensive disorders. Recently, vasodilators have also been used in the treatment of cardiac insufficiency, based on their action to reduce peripheral vascular resistance, as reported by Kei Itoh et al. (Nippon Rinsho, 36(11)51(1978)) and by Shinobu Matsui et al. (Abstract No.165, The 43rd annual congress of the Japanese Circulation Society).

DISCLOSURE OF THE INVENTION

The inventors conceived that cardiovascular diseases, as mentioned above, are related to one another and that the optimal treatment of these diseases would be such treatment as to improve these diseases comprehensively. As a result of a search for compounds that suit for this purpose, the inventors have found that 7-diethylamino-5-methylthiazolo[5,4-d]pyrimidine possesses vasodilating action, hypotensive action, inhibitory action on platelet aggregation, and lowering action on cholesterol levels in blood.

The present invention relates to a compound of 7-diethylamino-5-methylthiazolo[5,4-d]pyrimidine which generally can be prepared according to the following:

4-diethylamino-6-mercapto-2-methyl-5-nitropyrimidine is reduced according to the known methods to change the nitro group at the 5-position to an amino group. The aminopyrimidine derivative thus obtained is directly cyclized using formic acid to obtain the thiazolopyrimidine derivative.

The compound of this invention as obtained above may be converted to pharmacologically acceptable salt which is exemplified by acid adduct with inorganic acids, for instance, hydrochloric acid, hydrobromic acid, hydroiodic acid, sulphuric acid, nitric acid or phosphoric acid, or organic acids, for instance, acetic acid, maleic acid, citric acid, tartaric acid, oxalic acid or succinic acid.

The compound of this invention possesses favorable characteristics for a therapeutic agent, especially for a vasodilator, since it has potent vasodilating action, hypotensive action, inhibitory action on platelet aggregation and reducing action on blood cholesterol levels, and furthermore, is soluble in water. Thus, the composition that is related to the present invention or its acid adducts may be formulated to products which can be therapeutically used, alone or together with other pharmacologically active compounds, by any of the conventional methods, optionally using a pharmaceutically acceptable binder, filler or fragrances.

Now, an example of the process for preparing compound of the present invention will be shown below.

EXAMPLE 1

7-diethylamino-5-methylthiazolo[5,4-d]pyrimidine 7.3 g of 4-chloro-6-diethylamino-2-methyl-5-nitropyrimidine was dissolved in 100 ml of mixture of methanol-water (9:1), and 4.7 g of 70% sodium hydrosulfide was slowly added. The reaction mixture was stirred at room temperature for 30 minutes, and the solvent was distilled off under reduced pressure, and the pH of the residue was adjusted to 5–6 by adding 5N hydrochloric acid. Precipitated yellow crystals were filtered off by filtration. The crystals were recrystallized from a mixture of chloroform and n-hexane to obtain purified 4-diethylamino-6-mercapto-2-methyl-5-nitropyrimidine (5.2 g, melting point 181.3°~183.3° C.).

5 g of the crystals of 4-diethylamino-6-mercapto-2-methyl-5-nitropyrimidine and 7.0 g of metal tin were mixed well, and 50 ml of concentrated hydrochloric acid was slowly added to the mixture under cooling. After the addition, the reaction mixture was stirred at room temperature for 3 hours. Then 3N solution of sodium hydroxide was added to the mixture, while cooling with ice, and the pH of the mixture was adjusted to 8–9 to obtain an oily substance. The oily substance was extracted with 200 ml of ethyl acetate, and the organic layer was dried over magnesium sulphate anhydride. Then the solvent was distilled off under reduced pressure, and the residue was recrystallized from a mixture of chloroform and n-hexane to obtain crystals of 5-amino-4-diethylamino-6-mercapto-2-methylpyrimidine (3.9 g).

3 g of 5-amino-4-diethylamino-6-mercapto-2-methylpyrimidine was dissolved in 50 ml of 90% formic acid and refluxed for 2 hours. After the completion of the reaction, formic acid was distilled off under reduced pressure. The residue was added with 30 ml of water, and neutralized with ammonium hydroxide. This aqueous solution was extracted with 200 ml of ethyl acetate and the organic layer was dried over sodium sulphate anhydride. Then the solvent was distilled off under reduced pressure, and the residue was purified by column chromatography on silica-gel to obtain 7-diethylamino-5-methylthiazolo[5,4-d]pyrimidine (1.6 g).

Melting point: 41.6°–43° C.

Mass spectrum: M+ 222

Element analysis: $C_{10}H_{14}N_4S$ Calcd. C: 54.05%, H: 6.37%, N: 25.23%: Found. C: 54.11%, H: 6.32%, H: 25.29%.

NMR($\delta$ppm, $CDCL_3$) 8.48 1H s, 3.91 4H q(7 Hz), 2.49 3H s, 1.36 6H t(7 Hz)

What is claimed is:

1. A compound defined as 7-diethylamino-5-methyl-thiazolo[5,4-d]pyrimidine and its pharmacologically acceptable salts.

2. A therapeutic composition comprising a cardiovascular disease treating effective amount of 7-diethylamino-5-methylthiazolo[5,4-d] pyrimidine or its pharmacologically acceptable salts and a pharmaceutically acceptable carrier.

* * * * *